United States Patent [19]

Rasshofer et al.

[11] 4,384,102

[45] May 17, 1983

[54] PROCESS FOR THE PREPARATION OF COMPOUNDS HAVING S-TRIAZINE UNITS AND EPOXIDE GROUPS

[75] Inventors: Werner Rasshofer, Cologne; Gerhard Grögler, Leverkusen; Richard Kopp, Cologne, all of Fed. Rep. of Germany

[73] Assignee: Bayer Aktiengesellschaft, Leverkusen, Fed. Rep. of Germany

[21] Appl. No.: 336,659

[22] Filed: Jan. 4, 1982

[30] Foreign Application Priority Data

Jan. 8, 1981 [DE] Fed. Rep. of Germany ....... 3100355

[51] Int. Cl.³ .............................................. C08G 18/77
[52] U.S. Cl. ..................... 528/73; 524/872; 544/197; 544/204; 544/205; 544/206; 544/207; 544/208; 544/209
[58] Field of Search .................. 528/73; 544/197, 204, 544/205, 206, 207, 208, 209

[56] References Cited

U.S. PATENT DOCUMENTS

| | | | |
|---|---|---|---|
| 2,838,511 | 6/1958 | Kogon | 544/221 |
| 3,210,339 | 10/1968 | Schwarze et al. | 544/204 |
| 4,255,570 | 3/1981 | Grögler et al. | 544/197 |
| 4,348,512 | 9/1982 | Grogler et al. | 528/73 |

FOREIGN PATENT DOCUMENTS 955511 4/1964 United Kingdom .

*Primary Examiner*—John Kight, III
*Assistant Examiner*—Marvin L. Moore
*Attorney, Agent, or Firm*—Gene Harsh; Joseph C. Gil; Lyndanne M. Whalen

[57] ABSTRACT

Compounds having both s-triazine units and epoxide groups present are prepared by reacting an epoxide containing an isocyanate-reactive group with a triisocyanate corresponding to the formula:

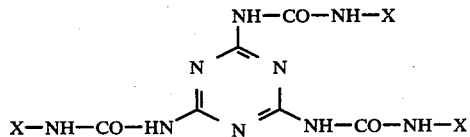

in which X is as defined herein. These reactants are used in quantities such that the equivalent ratio of isocyanate groups to isocyanate-reactive groups is maintained at less than or equal to 1 to 1. The compounds thus produced are particularly useful as reactive cross-linkers in the production of polyurethanes and polyepoxides.

7 Claims, No Drawings

PROCESS FOR THE PREPARATION OF COMPOUNDS HAVING S-TRIAZINE UNITS AND EPOXIDE GROUPS

BACKGROUND OF THE INVENTION

This invention relates to a process for the preparation of compounds having s-triazine units and epoxide groups.

Polyisocyanates containing s-triazine units obtained by the reaction of melamine with excess quantities of aromatic diisocyanates containing isocyanate groups with differing reactivities are described in European Pat. No. 893 (corresponding to U.S. Ser. No. 930,611 filed Aug. 3, 1978 now U.S. Pat. No. 4,255,570). The compounds described therein are solid substances which have very high melting points and are sparingly soluble to insoluble in organic media. The high melting points and poor solubility of these polyisocyanates severely limits their usefulness as reactive fillers in the production of polyurethanes by the isocyanate polyaddition process.

SUMMARY OF THE INVENTION

It is an object of the present invention to provide a process for the production of compounds containing both s-triazine units and epoxide groups.

It is another object of the present invention to provide a process for the production of compounds useful as reactive filler materials in the production of isocyanate resins.

It is also an object of the present invention to provide a process for the production of compounds containing both s-triazine units and epoxide groups which compounds melt at comparatively low temperatures (i.e., less than 300° C.) and/or are soluble in or compatible with materials used in the production of polyurethanes.

These and other objects which will be apparent to those skilled in the art are accomplished by reacting epoxide containing an isocyanate-reactive group with a triisocyanate corresponding to the formula:

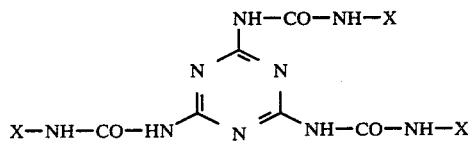

in which X represents a group obtained by removal of the more highly reactive of the isocyanate groups present in an aromatic diisocyanate having isocyanate groups of differing reactivities. These reactants are employed in amounts such that the equivalent ratio of isocyanate groups to isocyanate-reactive groups is maintained at less than or equal to 1 to 1.

DETAILED DESCRIPTION OF THE INVENTION

The present invention relates to a process for the preparation of compounds containing s-triazine units and epoxide groups in which triisocyanates corresponding to the formula:

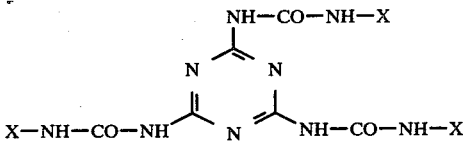

wherein
X denotes a group such as is obtained by the removal of the more highly reactive isocyanate group from an aromatic diisocyanate whose isocyanate groups differ in their reactivity (with respect to the isocyanate addition reaction)
are reacted with epoxide compounds containing isocyanate reactive groups in amounts such that an equivalent ratio of isocyanate groups to isocyanate-reactive groups of ≦1:1 is maintained.

In the process of the present invention, polyisocyanates containing s-triazine units corresponding to the above-mentioned formula are used as a starting material. Polyisocyanates of the given formula in which X denotes a 3-isocyanato-4-methylphenyl group or a 4-(2-isocyanatobenzyl)-phenyl group are particularly preferred reactants. The preparation of such polyisocyanates is described in European Pat. No. 893 and U.S. Ser. No. 930,611, filed Aug. 3, 1978, now U.S. Pat. No. 4,255,570. Specific polyisocyanates with s-triazine units suitable for the process of the present invention include N,N',N"-tri-(3-isocyanato-4-methylphenyl-aminocarbonyl)-melamine and N,N',N"-tri-[4-(2-isocyanatobenzyl)-phenyl-amino-carbonyl]-melamine.

The other reactants used in the process of the present invention may be any epoxide compound which in addition to epoxide groups contains at least 1 group capable of reacting in the isocyanate addition reaction and which has a molecular weight of from 74 to 1,000 (preferably from 74 to 500). Preferred epoxide compounds are those which have one epoxide group and one isocyanate-reactive group. An alcoholic hydroxyl group is a particularly preferred isocyanate-reactive group. Suitable epoxide group containing reactants are 2,3-epoxy-1-alkanols, glycidyl esters of hydrocarboxylic acids and monoglycidyl ethers of polyhydric alcohols. Among the 2,3-epoxy-1-alkanols which may be used are glycidol (2,3-epoxy-1-propanol) and its low molecular weight autocondensation products; and 2,3-epoxy alcohols such as 2,3-epoxy-1-butanol, 2,3-epoxy-1-pentanol, 2,3-epoxy-2-methyl-1-butanol and their low molecular weight autocondensation products.

Glycidyl esters of hydroxycarboxylic acids which may be used in the process of the present invention include the esters of lactic acid, glycolic acid, hydroxypivalic acid, 4-(2-hydroxyethoxy)-benzoic acid and 3-chloro-4-(2-hydroxyethoxy)-benzoic acid.

Specific examples of monoglycidyl ethers of polyhydric alcohols which may be employed are the ethers of alkanediols or alkenediols, such as ethylene glycol; 1,4-dihydroxybutane; di-, tri- and polyethylene glycols (molar mass up to about 800), glycerol, pentaerythritol and mannitol. Monoglycidyl ethers of polyvalent phenols such as hydroquinone, resorcinol, bisphenol-A or bisphenol-F may also be used but are less preferred. 2,3-epoxy-1-alkanols are particularly preferred, with glycidol being most preferred.

In the process of the present invention, the reactants should be used in amounts such that only products which contain no free isocyanate groups are formed.

That is, the polyisocyanates containing s-triazine units and the epoxide compounds containing isocyanate-reactive groups should be reacted in amounts such that the ratio of isocyanate-reactive groups to isocyanate groups is within the range of 1:1 to 10:1, preferably 1.1:1 to 5:1. Since the reactant containing epoxide groups is generally capable of being distilled and/or dissolved in the usual solvents (such as diethyl ether or acetone), any unreacted epoxide may be easily removed from the product of the present invention by distillation and/or extraction and/or filtration. The reactants used in the process of the present invention should generally be chosen so that the end products have a maximum molecular weight of about 4,000, preferably 2,500. If triisocyanates containing s-triazine units are reacted with compounds containing an epoxide group and a hydroxyl group, trifunctional epoxides are produced. The molecular weight of such epoxides may be calculated on the basis of their epoxide group content.

The process of the present invention may be carried out by reacting a mixture of a polyisocyanate corresponding to the above-given formula and at least one compound containing both epoxide groups and isocyanate-reactive groups for 2 to 100 hours (preferably 4 to 25 hours) with stirring. The process of the present invention should generally be carried out in the temperature range of from 0° C. to 100° C., preferably from 20° C. to 80° C. The reaction may be carried out with or without a solvent. A suitable solvent is one which is inert towards isocyanate groups, such as dioxane; tetrahydrofuran; benzene; toluene; chlorobenzene; dichlorobenzene; nitrobenzene; xylene; chlorinated aliphatic hydrocarbons; dipolar aprotic solvents such as N,N-dimethyl formamide, dimethyl sulphoxide, hexamethyl phosphoric acid triamide or sulpholan. Dimethyl formamide is a preferred solvent.

Accelerators for the isocyanate addition reaction known to those in the art may be used in the process of the present invention. Such accelerators include amidines such as diazabicyclo undecene, N-methyl-2-methyl-tetrahydropyrimidine; tertiary amines such as triethylene diamine (DABCO$^R$); and metal catalysts such as Sn-(II)-octoate, dibutyl tin dilaurate and lead octoate.

The products obtained from the process of the present invention are compounds generally containing from about 2.1 to 9 wt. %, preferably 4.2 to 9 wt. % s-triazine units and about 1.2 to 5.5 wt. %, preferably 1.9 to 5.5 wt. % epoxide oxygen. Since the products of the present invention are only slightly soluble in organic solvents at room temperature, they may be freed from starting compounds having excess epoxide groups by crystallization followed by washing with extracting agents such as diethyl ether or acetone.

The products of the process of the present invention have a wide range of melting points. The melting point is, of course, dependent upon the nature of the starting materials used. The products of the present invention differ from the starting polyisocyanates containing s-triazine units by their lower melting point and/or improved compatibility with starting materials conventionally used for the production of polyurethanes.

The products of the present invention are particularly suitable for use as a reactive cross-linker component in the production of polyurethanes because they are capable of being incorporated in the component containing isocyanate-reactive groups. The products of the process of the present invention may also be used as the sole isocyanate-reactive component in a reaction with organic polyisocyanates. The products of the present invention are also suitable as cross-linking agents for polyurethanes and polymers, which are used in the production of lacquers, adhesives, elastomers and foams. These products are also suitable as cross-linking components for the production of polyepoxides.

Having thus described our invention, the following examples are given by way of illustration. All percentages given in these examples are percents by weight unless otherwise indicated.

EXAMPLES

Example 1

Reaction of N,N',N''-tris-(3-isocyanato-4-methylphenylaminocarbonyl)-melamine with 2,3-epoxypropanol.

148 g of N,N',N''-tris-(3-isocyanato-4-methylphenylamino-carbonyl)-melamine (0.23 mol), 60 g of 2,3-epoxypropanol (0.81 mol) and 0.5 g of tin-2-ethyl hexanoate were suspended or dissolved in 200 ml of dimethyl formamide. The reaction mixture was stirred for 15 hours at 60° C. and then cooled to room temperature, suction filtered and washed with 150 ml of diethyl ether. After drying to constant weight at 15 Torr/50° C., 198 g of a colorless compound melting at 240° C. and containing 9% of s-triazine groups were obtained. The epoxide oxygen content was 5.3% (theoretical: 5.5%).

Example 2

Reaction of N,N',N''-tris-(3-isocyanato-4-methylphenylaminocarbonyl)-melamine with glycerol-1-glycidylether.

207 g of N,N',N''-tris-(3-isocyanato-4-methylphenylaminocarbonyl)-melamine (0.32 mol), 148 g of glycerol-1-glycidyl ether (1 mol) and 0.75 g of tin (II)-(2-ethyl-hexanoate) were suspended or dissolved in 200 ml of dimethyl formamide. The reaction mixture was stirred for 25 hours at 60° C., cooled to room temperature, suction filtered and washed with 150 ml of actone. After drying to constant weight at 15 Torr/50° C., 347 g of a colorless compound melting at 270° C. which contained 7.1% of s-triazine groups were obtained. The epoxide oxygen content was 4.3% (theoretical: 4.4%).

Example 3

50 g of an isocyanate prepolymer having an isocyanate content of 3.5% (obtained from tolylene-2,4-diisocyanate and a polypropylene ether glycol of molecular weight 2,000) were vigorously mixed with 12.5 g of the finely milled epoxide from Example 1 and 0.5 ml of boron trifluoride etherate and hardened for 3 hours at 130° C. A soft, tack-free polymer was obtained. A similar result was obtained when the same mixture was hardened at room temperature for 3 days.

Example 4

50 g of an isocyanate prepolymer having an isocyanate content of 2.67% (obtained from tolylene-2,4-diisocyanate and trifunctional propylene oxide/ethylene oxide polyether polyol of molecular weight 6,000 started on trimethylol propane) were vigorously mixed with 8 g of the finely milled epoxide from Example 1 and 0.5 ml of boron trifluoride etherate and hardened in an open metal mold for 3 hours at 130° C. A semi-rigid, tack-free elastic polymer was formed.

Example 5

50 g of the finely milled epoxide from Example 1 (57.5 m mol) vigorously mixed with 43.5 g of a semi-prepolymer having an isocyanate content of 18.3% (prepared by the reaction of (i) a polyisocyanate obtained by the phosgenation of aniline-formaldehyde condensates and having a viscosity of 130 mPas (25° C.) and an isocyanate content of 31% by weight with (ii) a polyether of OH number 42 obtained by the chemical addition of a mixture of propylene oxide and ethylene oxide to a mixture of trimethylol propane and propylene glycol (molar ratio 3:1) and 2.5 ml of boron trifluoride etherate. The mixture was introduced into an open mold having a diameter of 10 cm. The mass hardened within 2 hours at 130° C. to a rigid, tack-free polymer.

What is claimed is:

1. A process for the production of compounds having s-triazine units and epoxide groups comprising reacting an epoxide compound containing an isocyanate-reactive group with a triisocyanate corresponding to the formula:

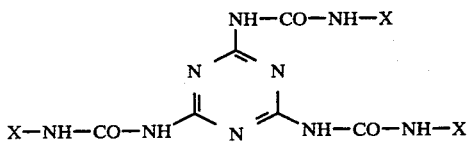

wherein
X represents a group obtained by removal of the more highly reactive of the isocyanate groups present in an aromatic diisocyanate having isocyanate groups of differing reactivities in an amount such that the equivalent ratio of isocyanate groups to isocyanate-reactive groups is maintained at less than or equal to 1 to 1.

2. The process of claim 1 wherein the epoxide compound containing isocyanate reactive groups is a 2,3-epoxy-1-alkanol.

3. The process of claim 2 wherein X denotes a 3-isocyanato-4-methylphenyl group or a 4-(2-isocyanatobenzyl)-phenyl group.

4. The process of claim 1 wherein X denotes a 3-isocyanato-4-methylphenyl group or a 4-(2-isocyanatobenzyl)-phenyl group.

5. A filler component useful in the production of polyurethanes which is a compound having s-triazine units and epoxide groups formed by reacting (a) a triisocyanate of the formula:

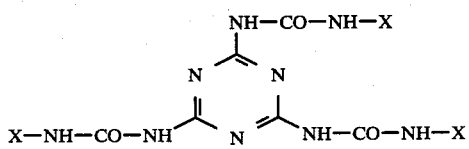

wherein
X denotes a group such as is obtained by the removal of the more highly reactive of the isocyanate groups from an aromatic diisocyanate having isocyanate groups of differing reactivities in the isocyanate addition reaction
with an epoxide compound containing isocyanate reactive groups in a manner such that the equivalent ratio of isocyanate groups to isocyanate reactive groups is $\leq 1:1$.

6. The filler component of claim 5 wherein the epoxide compound is 2,3-epoxy-propanol.

7. The filler component of claim 5 wherein the triisocyanate is N,N',N''-tris-(3-isocyanato-4-methylphenylaminocarbonyl)-melamine.

* * * * *